United States Patent
Balgobin et al.

(10) Patent No.: US 9,179,922 B2
(45) Date of Patent: Nov. 10, 2015

(54) METHOD OF MAKING INTERVENTIONAL MEDICAL DEVICE SYSTEM HAVING A SLOTTED SECTION AND RADIOPAQUE MARKER

(75) Inventors: Keith Balgobin, Pembroke Pines, FL (US); Vladimir Mitelberg, Austin, TX (US); Jason Rainer, Miramar, FL (US); John H. Thinnes, Jr., Miami Beach, FL (US)

(73) Assignee: DEPUY SYNTHES PRODUCTS, LLC, Raynham, MA (US)

( * ) Notice: Subject to any disclaimer, the term of this patent is extended or adjusted under 35 U.S.C. 154(b) by 853 days.

(21) Appl. No.: 13/469,375

(22) Filed: May 11, 2012

(65) Prior Publication Data

US 2012/0222286 A1    Sep. 6, 2012

Related U.S. Application Data

(62) Division of application No. 11/741,116, filed on Apr. 27, 2007, now Pat. No. 8,197,442.

(51) Int. Cl.
- *A61M 25/098* (2006.01)
- *B21D 39/04* (2006.01)
- *A61B 17/12* (2006.01)

(Continued)

(52) U.S. Cl.
CPC ........ *A61B 17/1214* (2013.01); *A61M 25/0108* (2013.01); *B21D 39/046* (2013.01); *A61B 17/00234* (2013.01); *A61B 17/12022* (2013.01); *A61B 19/36* (2013.01); *A61B 19/54* (2013.01); *A61B 2017/00292* (2013.01); *A61B 2017/00526* (2013.01); *A61B 2017/12054* (2013.01);

(Continued)

(58) Field of Classification Search
CPC ............... Y10T 29/49908; Y10T 29/49995; Y10T 29/49927; Y10T 29/49904; B21D 39/048; B21D 39/046; A61M 25/0051; A61M 25/0013; A61M 25/0012; A61M 25/0138; A61M 25/0108; A61B 2017/00526; A61B 2017/00292; A61B 17/00234
See application file for complete search history.

(56) References Cited

U.S. PATENT DOCUMENTS 4,938,220 A * 7/1990 Mueller, Jr. .................. 600/435
4,994,069 A   2/1991 Ritchart et al.

(Continued)

FOREIGN PATENT DOCUMENTS

CA        2 532 548        2/2005
WO    WO 2005/009523    2/2005

OTHER PUBLICATIONS

U.S. Appl. No. 11/461,231, filed Jul. 31, 2006, Mitelberg et al.

(Continued)

*Primary Examiner* — Jermie Cozart
(74) *Attorney, Agent, or Firm* — Cook Alex Ltd.

(57) ABSTRACT

A system is provided that includes an elongated introducer navigable through body vessels of a human subject and a pusher component for incorporation within the introducer. The pusher component includes a tubular portion with a slotted section. A radiopaque marker is secured to at least a portion of the slotted section such that an outer surface of the radiopaque marker is substantially flush with an outer surface of the tubular portion immediately proximal and/or immediately distal the radiopaque marker. According to a method of manufacturing such a component, the slotted section is formed by a laser cutting operation and a pre-assembly radiopaque marker member is crimped onto the slotted section.

20 Claims, 2 Drawing Sheets

(51) Int. Cl.
*A61M 25/01* (2006.01)
*A61M 25/00* (2006.01)
*A61B 17/00* (2006.01)
*A61B 19/00* (2006.01)

(52) U.S. Cl.
CPC ....... *A61M25/0012* (2013.01); *Y10T 29/49904* (2015.01); *Y10T 29/49908* (2015.01)

(56) References Cited

U.S. PATENT DOCUMENTS

| | | | |
|---|---|---|---|
| 5,485,667 A * | 1/1996 | Kleshinski | 29/447 |
| 5,800,455 A | 9/1998 | Palermo et al. | |
| 5,947,962 A | 9/1999 | Guglielmi et al. | |
| 6,179,811 B1 * | 1/2001 | Fugoso et al. | 604/96.01 |
| 6,238,340 B1 * | 5/2001 | Alt et al. | 600/431 |
| 6,520,934 B1 * | 2/2003 | Lee et al. | 604/103.1 |
| 2003/0121148 A1 | 7/2003 | DiCaprio et al. | |
| 2004/0093014 A1 | 5/2004 | Ho et al. | |
| 2004/0106913 A1 | 6/2004 | Eidenschink et al. | |
| 2007/0010849 A1 | 1/2007 | Balgobin et al. | |
| 2007/0287957 A1 * | 12/2007 | Magnuson et al. | 604/103.1 |
| 2009/0036768 A1 | 2/2009 | Seehusen et al. | |

OTHER PUBLICATIONS

U.S. Appl. No. 11/461,245, filed Jul. 31, 2006, Mitelberg et al.
European Search Report of European Patent Application EP 08 25 1375 (Patent 1985244), dated Mar. 10, 2010.

* cited by examiner

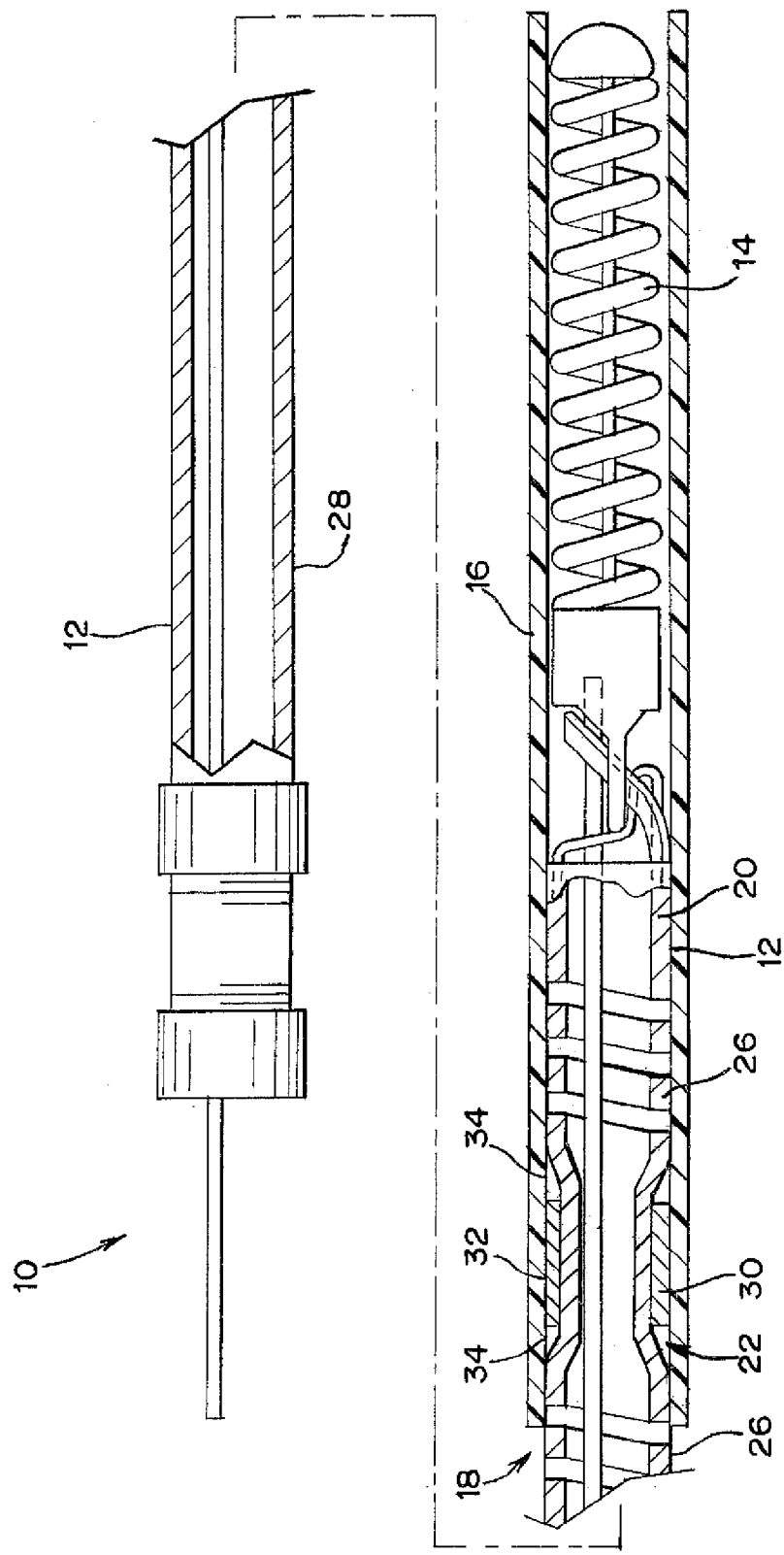

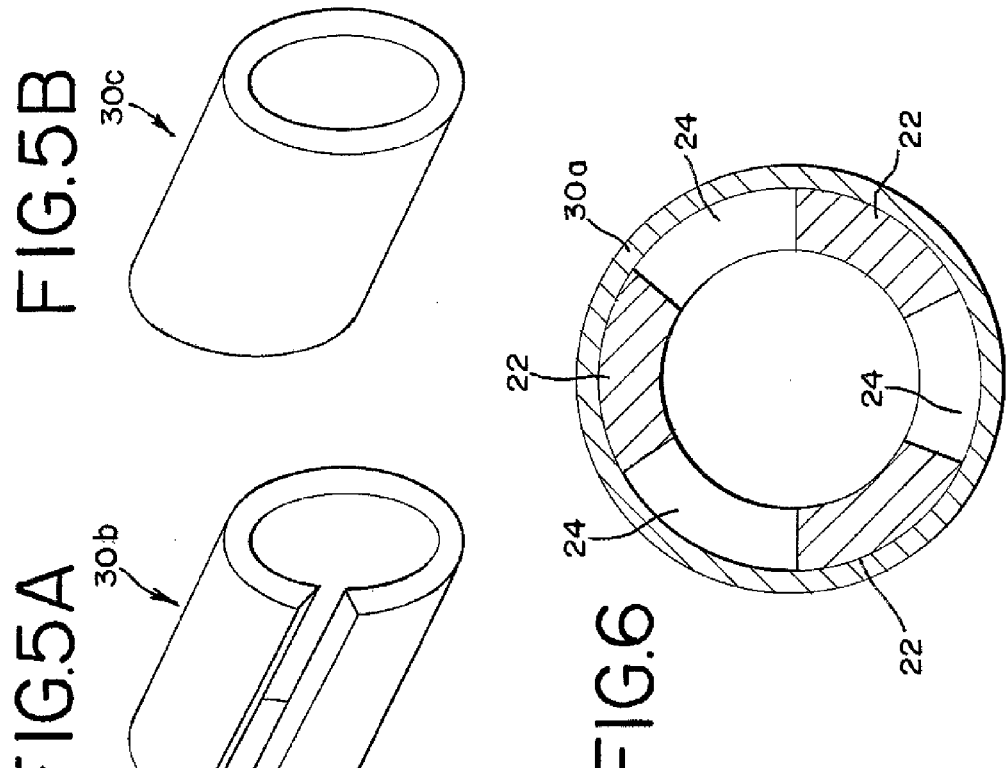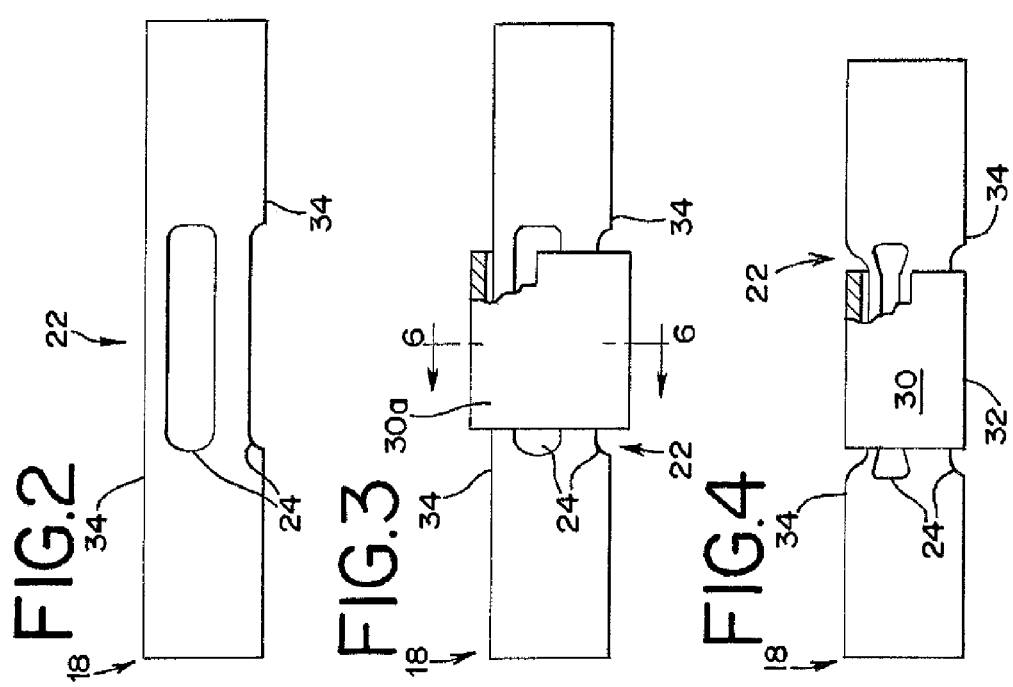

METHOD OF MAKING INTERVENTIONAL MEDICAL DEVICE SYSTEM HAVING A SLOTTED SECTION AND RADIOPAQUE MARKER

This is a divisional of U.S. patent application Ser. No. 11/741,116, filed Apr. 27, 2007, now U.S. Pat. No. 8,197,442 B2 hereby incorporated by reference hereinto.

DESCRIPTION

1. Field of the Invention

This invention generally relates to medical devices that are navigable through body vessels of a human subject. More particularly, this invention relates to tubular devices having a slotted section and radiopaque marker and methods of making the same.

2. Description of Related Art

A number of medical procedures require the introduction of tubing to a body vessel. For example, vessel defects, such as blockages and stenoses, within the human vasculature system are often treated by the intraluminal delivery of treatment fluids or implants, such as expandable stents and embolic coils. Implants can take any of a number of forms and may be delivered to a diseased site in a number of manners. According to one known method of delivering a medical implant, the distal end of a flexible catheter is positioned adjacent to a target site of a body vessel, such as an aneurysm. Once the catheter is properly positioned, a delivery/detachment system is passed through a lumen of the catheter until a distal end of the delivery system exits the distal end of the catheter in the area of the target site. An implant, such as an embolic coil, carried at the distal end of the delivery/detachment system is thereafter released to the diseased site.

The path to the target site is typically tortuous, so the catheter is preferably relatively flexible to allow it to pass through the vasculature to the desired site. Conversely, the catheter may be required to pass through constricted vessels, so it is also desirable for it to exhibit good column strength. When the catheter has been properly positioned, the delivery system must follow the path defined by the catheter, so the delivery system also preferably has similar characteristics of flexibility and good column strength. In particular, it is generally preferred for the delivery system to exhibit column strength and good pushability, particularly at its proximal end, to allow the delivery system to be pushed through the catheter, and relatively flexible especially at a distal end, to allow the delivery system to follow the path defined by the catheter.

It may also be preferred to provide the catheter and/or the delivery system with one or more radiopaque markers, typically positioned at the distal end thereof, to aid in the positioning and deployment of the implant to a target location within a body vessel. The implant itself may also be provided with a radiopaque marker. Radiopaque markers facilitate the positioning of the implant within a blood vessel by allowing a physician to determine the exact location and orientation of the catheter, delivery system, and/or implant under x-ray or fluoroscopy. These markers are typically formed of a radiopaque material such as tantalum, zirconium, gold, platinum, iridium, tungsten, or a combination thereof.

For a radiopaque marker applied to certain medical device components, an important objective may be to have the marker be substantially flush with an outer surface of the component. For example, as described previously, an implant delivery system is pushed through a catheter to deliver an implant to a target location within a body vessel. If the distal end of the delivery system has a radiopaque marker extending beyond the outer surface of the system, it creates a projecting discontinuity or "ledge," which increases the risk that the projecting marker will promote potentially undesirable contact with a guiding catheter, other component of the system, a body vessel wall or the like. In the case of a marker band that imparts a projecting discontinuity (which can be circumferential in the case of a band that extends the full circumferential extent of the device), there is a potential risk of some adverse effect, no matter how minimal, or of interference with a fully smooth operation of the diagnostic or treatment system, such as by snagging upon a catheter as it is pushed therethrough to the target location. It will be appreciated by those of ordinary skill in the art that other medical device components may similarly benefit from a radiopaque marker that is flush with the outer surface of the component.

A general aspect or object of the present invention is to provide a medical device system that includes a component having a radiopaque marker which avoids the creation of a "ledge" that may adversely affect performance of the component within an introducer or catheter through which the component is administered.

Another aspect or object of this invention is to provide a method of affixing a radiopaque marker to a medical device component so as to avoid the creation of a "ledge" that may adversely affect performance of that component within an introducer or catheter through which the component is administered.

Other aspects, objects and advantages of the present invention, including the various features used in various combinations, will be understood from the following description according to preferred embodiments of the present invention, taken in conjunction with the drawings in which certain specific features are shown.

SUMMARY

In accordance with one embodiment or aspect of the present invention, a component of an interventional medical device system operable while within a body vessel includes an elongated introducer within which is positioned a pusher that is provided with a generally hollow tubular portion. The tubular portion includes a slotted section. An arcuate radiopaque marker overlays at least a portion of the slotted section. An outer surface of the radiopaque member is substantially flush with an outer surface of the tubular portion immediately proximal or immediately distal the radiopaque marker.

According to another aspect or embodiment of the present invention, a component of an interventional medical device system operable while within a body vessel includes an elongated introducer within which is positioned a pusher that is provided with a generally hollow metallic tubular portion. The tubular portion includes a slotted section having three longitudinal slots equally spaced from each other about a circumference of the slotted section. A substantially tubular radiopaque marker encircles at least a portion of the three slots. An outer surface of the radiopaque member is substantially flush with an outer surface of the tubular portion immediately proximal and immediately distal the radiopaque marker.

According to yet another aspect or embodiment of the present invention, a method of creating a component of an interventional medical device system that includes an elongated introducer and a pusher component therewithin, the system being operable while within a body vessel is provided that includes providing a tubular member and forming at least one slot in the tubular member. A pre-assembly radiopaque marker member then is positioned over at least a portion of the slot. The pre-assembly radiopaque marker member is crimped onto the slot such that an outer surface of the thus formed radiopaque member is substantially flush with an outer surface of the tubular portion immediately proximal or immediately distal of the radiopaque marker.

Special application for the present invention has been found for tubular portions of medical device guidewires, catheters, microcathers, fine-bore guiding cathers, and embolic coil/implant delivery, detachment or retrieval systems. Suitable medical procedure applications are illustrated in U.S. patent application Ser. Nos. 11/461,231 and 11/461,245 to Mitelberg et al., filed Jul. 31, 2006, now respectively U.S. Pat. No. 8,366,720 B2 and U.S. Pat. No. 8,062,325 B2 which are hereby incorporated herein by reference. However, the present invention is also applicable to tubular components of other devices adapted for movement through body lumens, so it will be understood that certain embodiments of the products and methods described herein are not limited to particular medical devices or particular surgical applications.

BRIEF DESCRIPTION OF THE DRAWINGS

FIG. 1 is partial cross-sectional view of an implantable medical device delivery system incorporating an elongated introducer and a medical device component according to an aspect of the present invention;

FIG. 2 is a side elevational view of a tubular portion of a component according to an aspect of the present invention;

FIG. 3 is a side elevational view of the tubular portion of FIG. 2, associated with a pre-assembly radiopaque marker member in a disconnected condition, a portion of the pre-assembly radiopaque marker member being broken away for clarity;

FIG. 4 illustrates the tubular portion and radiopaque marker of FIG. 3, with the radiopaque marker in a connected condition, a portion of the radiopaque marker being broken away for clarity;

FIG. 5A is a front perspective view of an embodiment of a pre-assembly radiopaque marker member according to an aspect of the present invention;

FIG. 5B is a front perspective view of another embodiment of a pre-assembly radiopaque marker member according to an aspect of the present invention; and FIG. 6 is a cross-sectional view of the tubular portion and pre-assembly radiopaque marker member of FIG. 3, taken through the line 6-6 of FIG. 3.

DESCRIPTION OF THE ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 shows an interventional medical device system 10 operable while within a body vessel. The illustrated system 10 is an embolic coil delivery system and operates generally according to the description found in U.S. Patent Application Publication No. 2007/0010849 to Balgobin et al., which is hereby incorporated herein by reference. The illustrated system 10 is merely exemplary of an interventional medical device in which a medical device component according to the present invention may be incorporated and other devices may be employed without departing from the scope of the present invention.

The system 10 includes a pusher member 12, which is an exemplary medical device component according to the present invention. The pusher member 12 is a generally hollow tube or tubular structure used to push an embolic coil 14 through an introducer or catheter 16 of the system 10. When used herein, the terms "tubular" and "tube" are to be construed broadly and are not limited to a structure that is a right cylinder or strictly circumferential in cross-section or of a uniform cross-section throughout its length. For example, the pusher member 12 is shown as a substantially right cylindrical structure. However, the pusher member 12 may have a tapered or curved outer surface without departing from the scope of the present invention.

The pusher member 12 includes a generally hollow tubular portion 18, illustrated in FIG. 1 at a distal end 20 thereof, with a slotted section 22. The slotted section 22 comprises at least one slot 24, as shown in FIG. 2. In the embodiment of FIG. 1, the distal end 20 of the pusher member 12 has a spiral ribbon 26 at opposite ends of the slotted section 22, which provides flexibility that may be advantageous for moving the pusher member 12 through the catheter 16. Typically, it is preferred for at least the proximal end 28 of the pusher member 12 to exhibit good column strength, so the pusher member 12 may comprise a metal hypotube, with the proximal end 28 being a non-slotted, non-spiral section.

According to one method of forming the slotted section 22, a generally hollow tubular member and a cutting device are provided. The nature of the cutting device depends on the material of the hollow tubular member, but a laser is a suitable cutting device for use with a metallic tubular member, such as a hypotube. In the case of a stainless steel tubular member suitable for use in delivering a neurovascular implant, i.e. a tubular member having an outer diameter no greater than 0.025 inch, the laser may be adapted to provide a kerf in the range of about 0.005 inch to about 0.015 inch (a specific example being 0.010 inch). The slots 24 are formed by cutting openings into the slotted section 22.

When using a laser, the slots may be formed one or two at a time. To form a single slot, the laser may be applied to the slotted section along a line generally tangential to the wall of the tubular member. To form two slots in a slotted section, a pair of tangentially directed lasers may be employed, with each laser separately forming one slot. In yet another embodiment, a single laser may be applied to the slotted section along a line generally transverse to and through the longitudinal axis of the tubular member. The laser will cut through the wall of the tubular member to define a first slot, pass through the hollow interior, and cut through the wall on the other side of the tubular member to define a second slot in facing relationship to the first slot. If the slot is to be larger than the opening defined by the laser, the laser and/or the tubular member may be moved relative to the other while continuing to operate the laser to fully define the slot.

While cutting, and particulary laser-cutting, is one method of forming slots in the slotted section, other methods may be also be employed. For example, the slots may be formed by chemical etching or the like without departing from the scope of the present invention.

As shown in FIG. 1, the slotted section 22 is associated with a radiopaque marker 30. The radiopaque marker 30 may be comprised of any radiopaque material, including but not limited to tantalum, zirconium, gold, platinum, iridium, tungsten, or a combination thereof. The radiopaque marker 30 overlays at least a portion of the slotted section 22. The radiopaque marker 30, in a connected condition shown in FIG. 1 and described in greater detail herein, may be shorter than the slotted section 22 in a direction along the length of the medical device component, in which case the radiopaque marker 30 will overlay a portion of the slotted section 22 less than the total length of the slotted section 22. It may be advantageous for the radiopaque marker 30 to be only slightly shorter than the slotted section 22, because such a marker will provide improved visibility within a body vessel compared to a marker that is substantially shorter than the slotted section.

The radiopaque marker originates as a pre-assembly radiopaque marker member 30a, which is movable or transformable from a disconnected or pre-assembly condition, shown generally in FIG. 3, to a connected or assembled or fully assembled condition, shown generally in FIGS. 1 and 4. In the disconnected or pre-assembly condition, the pre-assembly radiopaque marker member 30a is placed against the outer surface of the slotted section 22, but the pre-assembly radiopaque marker member 30a will not be fixedly secured to the slotted section 22 or any portion thereof. Typically, a pre-assembly radiopaque marker member 30a in a disconnected condition is positioned over at least a portion of all of the slots 24 of the slotted section 22 (FIG. 3). For this reason, it may be advantageous for all of the slots 24 to be positioned at the same longitudinal location, spaced along the circumference of the slotted section 22, as shown in FIG. 2-4.

When the pre-assembly radiopaque marker member 30a is moved to the connected condition of FIGS. 1 and 4, it clamps down on the slotted section 22 as an assembled radiopaque marker 30 and will be substantially affixed to at least a portion of the slotted section 22. The pre-assembly radiopaque marker member 30a is preferably moved from the disconnected condition (FIG. 3) to the connected condition (FIG. 4) by a crimping operation. In one embodiment, the pre-assembly radiopaque marker member may be initially provided as a generally flat sheet or a C-shaped sheet of pre-assembly radiopaque material 30b as shown in FIG. 5A that is placed over a portion of the slotted section 22 and crimped therearound so as to overlay it and be fixedly secured thereto as an assembled radiopaque marker 30. A radiopaque marker 30 so secured to the slotted section 22 may be substantially arcuate, typically defining an arc greater than 180° to ensure that the radiopaque marker 30 remains secured to the slotted section 22. More typically, the radiopaque marker 30 may define an arc substantially greater than 180° when secured to the slotted section 22, for example in the range of approximately 300° to approximately 330°, for improved visualization when the interventional medical device 10 is within a body vessel. Most advantageously, the sheet 30b is adapted such that it will be substantially tubular, preferably without overlapping edges, and substantially encircle at least a portion of the slotted section 22 in the connected condition. A radiopaque marker having a tubular configuration may be advantageous because such a radiopaque marker is viewable under x-ray or fluoroscopy regardless of the position of the component in a body vessel.

In one embodiment, illustrated in FIG. 5B, a pre-assembly radiopaque marker member 30c is initially provided in a substantially tubular configuration and substantially encircles at least a portion of the slotted section 22 when subsequently moved to the connected condition. When used herein, the term "arcuate" applies to both partially tubular radiopaque markers (i.e., those defining an arc less than 360° when secured to the slotted section) and tubular radiopaque markers (i.e., those defining a 360° arc when secured to the slotted section). A pre-assembly radiopaque marker member 30c initially provided according to the configuration of FIG. 5B may be advantageous because the crimping operation may be carried out automatically by a swaging machine according to known design. One exemplary swaging machine which is suitable for use with a substantially tubular pre-assembly radiopaque marker member 30c is the model MBS-140CR marker band swager from Interface Associates of Laguna Niguel, Calif.

As shown in FIGS. 1 and 4, the radiopaque marker 30 will radially compress the portion of the slotted section 22 which it overlays. To promote uniform radial compression, it may be advantageous to provide a plurality of substantially identical slots 24, position them at the same longitudinal location, and space the slots 24 along the circumference of the slotted section 22, with adjacent slots 24 being equally spaced from each other. For example, FIG. 6 is a cross-sectional view of the slotted section 22 of FIG. 3, which shows an embodiment having three slots 24 equally spaced from each other about the circumference of the slotted section 22. As perhaps best illustrated in FIG. 2, it may be to further advantage for the slots 24 to be longitudinally elongated, referred to herein as "longitudinal slots," which decreases the compressive radial force required to partially collapse the slotted section 22.

Advantageously, the radiopaque marker 30 will compress the slotted section 22 to the extent that the outer surface 32 of the radiopaque member 30 is substantially flush with the outer surface 34 of the tubular portion 18 immediately proximal or immediately distal the radiopaque marker 30. More typically, the outer surface 32 of the radiopaque marker 30 is substantially flush with the outer surface 34 of the tubular portion 18 immediately proximal and immediately distal the radiopaque marker 30, as shown in FIGS. 1 and 4.

When the ends of the radiopaque marker 30 are substantially flush with the sections of the tubular portion 18 immediately adjacent thereto, there will be no regions of projecting discontinuity or "ledges" created. If the component is a pusher member of an embolic coil delivery/detachment system, as shown in FIG. 1, the lack of "ledges" promotes smooth movement of the device through a catheter or introducer. Other advantages may also be achieved by such a configuration, depending upon the nature of the interventional medical device and the anticipated use thereof.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:
1. A method of manufacturing an interventional medical device system operable while within a body vessel, comprising:
    providing a generally hollow tubular member;
    forming at least one slot in the tubular member;
    providing a pre-assembly radiopaque marker member;
    positioning the pre-assembly radiopaque marker member over at least a portion of said at least one slot;
    crimping the pre-assembly radiopaque marker member onto said at least one slot to form pusher member with a radiopaque marker such that an outer surface of the thus crimped radiopaque member is substantially flush with an outer surface of the tubular portion immediately proximal or immediately distal of the radiopaque marker; and positioning said pusher member with radiopaque marker into the lumen of an elongated introducer to provide the interventional medical device system.

2. The method of claim 1, further comprising providing a cutting device, wherein said forming at least one slot includes cutting at least one slot in the tubular member.

3. The method of claim 1, wherein said crimping the pre-assembly radiopaque marker member onto said at least one slot includes crimping the pre-assembly radiopaque marker member onto said at least one slot such that the thus crimped radiopaque marker defines an arc greater than 180°.

4. The method of claim 1, wherein said crimping the pre-assembly radiopaque marker member onto said at least one slot includes crimping the pre-assembly radiopaque marker member onto said at least one slot such that the thus crimped radiopaque marker substantially encircles at least a portion of said tubular member.

5. The method of claim 1, wherein said crimping the pre-assembly radiopaque marker member onto said at least one slot includes crimping the pre-assembly radiopaque marker member onto said at least one slot such that the outer surface of the thus crimped radiopaque marker is substantially flush with the outer surface of the tubular portion immediately proximal and immediately distal of the radiopaque marker.

6. The method of claim 1, wherein said providing a generally hollow tubular member includes providing a tubular member substantially comprised of a metallic material.

7. The method of claim 1, wherein said forming at least one slot includes forming a plurality of slots in the tubular member, said positioning the pre-assembly radiopaque marker member over at least a portion of said at least one slot includes positioning the pre-assembly radiopaque marker member over at least a portion of all of said plurality of slots, and said crimping the pre-assembly radiopaque marker member onto said at least one slot includes crimping the pre-assembly radiopaque marker member onto all of said plurality of slots such that an outer surface of the thus crimped radiopaque member is substantially flush with an outer surface of the tubular portion immediately proximal or immediately distal of the radiopaque marker.

8. The method of claim 7, wherein said forming at least one slot includes forming a plurality of slots in the tubular member such that adjacent slots are equally spaced from each other about a circumference of the tubular member.

9. The method of claim 1, wherein said forming at least one slot includes forming three substantially identical longitudinal slots in the tubular member, said positioning the pre-assembly radiopaque marker member over at least a portion of said at least one slot includes positioning the pre-assembly radiopaque marker member over at least a portion of said three longitudinal slots, and said crimping the pre-assembly radiopaque marker member onto said at least one slot includes crimping the pre-assembly radiopaque marker member onto said three longitudinal slots such that an outer surface of the thus crimped radiopaque member is substantially flush with an outer surface of the tubular portion immediately proximal or immediately distal of the radiopaque marker.

10. The method of claim 9, wherein said forming at least one slot includes forming three substantially identical longitudinal slots equally spaced from each other about a circumference of the tubular member.

11. A method for manufacturing an interventional medical device system operable while within a body vessel, comprising:
providing an elongated introducer having a lumen, the introducer being for administration within a body vessel;
positioning a pusher component within the lumen of the elongated introducer, the pusher component including a generally hollow tubular portion;
forming at least one slot in the tubular portion;
providing a pre-assembly radiopaque marker;
fixedly securing by clamping down and radially compressing the pre-assembly radiopaque marker having an outer surface to at least a portion of the slotted section such that the radiopaque marker is in a connected condition, including partially collapsing the slotted section; and
thereby providing a connected condition at which the outer surface of the radiopaque marker on the partially collapsed slotted section of the pusher component is substantially flush with an outer surface of the tubular portion immediately proximal of the radiopaque marker, immediately distal of the radiopaque marker, or both immediately proximal and immediately distal of the radiopaque marker.

12. The method of claim 11, further comprising providing a cutting device, wherein said forming at least one slot includes cutting at least one slot in the tubular member.

13. The method of claim 11, wherein said crimping the pre-assembly radiopaque marker member onto said at least one slot includes crimping the pre-assembly radiopaque marker member onto said at least one slot such that the thus crimped radiopaque marker defines an arc greater than 180°.

14. The method of claim 11, wherein said forming at least one slot includes forming a plurality of slots in the tubular member, said positioning the pre-assembly radiopaque marker member over at least a portion of said at least one slot includes positioning the pre-assembly radiopaque marker member over at least a portion of all of said plurality of slots, and said crimping the pre-assembly radiopaque marker member onto said at least one slot includes crimping the pre-assembly radiopaque marker member onto all of said plurality of slots such that an outer surface of the thus crimped radiopaque member is substantially flush with an outer surface of the tubular portion immediately proximal or immediately distal of the radiopaque marker.

15. The method of claim 11, wherein said forming at least one slot includes forming three substantially identical longitudinal slots in the tubular member, said positioning the pre-assembly radiopaque marker member over at least a portion of said at least one slot includes positioning the pre-assembly radiopaque marker member over at least a portion of said three longitudinal slots, and said crimping the pre-assembly radiopaque marker member onto said at least one slot includes crimping the pre-assembly radiopaque marker member onto said three longitudinal slots such that an outer surface of the thus crimped radiopaque member is substantially flush with an outer surface of the tubular portion immediately proximal or immediately distal of the radiopaque marker.

16. A method for manufacturing an interventional medical device system operable while within a body vessel, comprising:
providing an elongated introducer having a lumen, the introducer being for administration within a body vessel;
positioning a pusher component within the lumen of the elongated introducer, the pusher component having a longitudinal axis and including a generally hollow tubular portion;
forming a plurality of longitudinal slots in the tubular position each having a length greater than a width thereof, the length being substantially parallel to the pusher component longitudinal axis;
providing a pre-assembly radiopaque marker;

fixedly securing by clamping down and radially compressing the pre-assembly radiopaque marker having an outer surface and an inner surface, said fixedly securing including overlaying and fixedly securing to at least a portion of the outer surface of the slotted section, such that the radiopaque marker is in a connected condition at which the marker inner surface engages the slotted section outer surface thereby clamping the marker down on and radially compressing same and thus partially collapsing the slotted section; and thereby providing a connected condition at which the outer surface of the radiopaque marker is on the partially collapsed slotted section outer surface and dimensionally reduced from a pre-assembly, radiopaque marker member that is dimensionally larger than the marker outer surface as thus assembled onto the slotted section outer surface, and the marker at its connected condition is substantially flush with an outer surface of the tubular portion immediately proximal of the radiopaque marker, immediately distal of the radiopaque marker, or both immediately proximal and immediately distal of the radiopaque marker.

17. The method of claim 16, further comprising providing a cutting device, wherein said forming at least one slot includes cutting at least one slot in the tubular member.

18. The method of claim 16, wherein said crimping the pre-assembly radiopaque marker member onto said at least one slot includes crimping the pre-assembly radiopaque marker member onto said at least one slot such that the thus crimped radiopaque marker defines an arc greater than 180°.

19. The method of claim 16, wherein said forming at least one slot includes forming a plurality of slots in the tubular member, said positioning the pre-assembly radiopaque marker member over at least a portion of said at least one slot includes positioning the pre-assembly radiopaque marker member over at least a portion of all of said plurality of slots, and said crimping the pre-assembly radiopaque marker member onto said at least one slot includes crimping the pre-assembly radiopaque marker member onto all of said plurality of slots such that an outer surface of the thus crimped radiopaque member is substantially flush with an outer surface of the tubular portion immediately proximal or immediately distal of the radiopaque marker.

20. The method of claim 16, wherein said forming at least one slot includes forming three substantially identical longitudinal slots in the tubular member, said positioning the pre-assembly radiopaque marker member over at least a portion of said at least one slot includes positioning the pre-assembly radiopaque marker member over at least a portion of said three longitudinal slots, and said crimping the pre-assembly radiopaque marker member onto said at least one slot includes crimping the pre-assembly radiopaque marker member onto said three longitudinal slots such that an outer surface of the thus crimped radiopaque member is substantially flush with an outer surface of the tubular portion immediately proximal or immediately distal of the radiopaque marker.

* * * * *